United States Patent [19]
Campion et al.

[11] Patent Number: 4,784,655
[45] Date of Patent: Nov. 15, 1988

[54] EXTERNAL CATHETER AND APPLICATOR

[75] Inventors: Terese A. Campion, Waterbury, Conn.; Hitoshi Sawantani, Osaka, Japan

[73] Assignee: Sherwood Medical Company, St. Louis, Mo.

[21] Appl. No.: 21,464

[22] Filed: Mar. 4, 1987

[51] Int. Cl.⁴ .............................................. A61F 5/44
[52] U.S. Cl. ...................................................... 604/349
[58] Field of Search ............................... 604/349–353; 128/132 R

[56]  References Cited
U.S. PATENT DOCUMENTS

| | | | |
|---|---|---|---|
| 3,369,546 | 2/1968 | Hickok | 604/349 |
| 3,520,305 | 7/1970 | Davis | 604/349 |
| 4,475,909 | 10/1984 | Eisenberg | 604/349 |
| 4,475,910 | 10/1984 | Conway et al. | 604/349 |
| 4,540,409 | 9/1985 | Nystrom et al. | 604/349 |
| 4,589,874 | 5/1986 | Riedel et al. | 604/349 |

FOREIGN PATENT DOCUMENTS 2410697 12/1974 Fed. Rep. of Germany ...... 604/349

Primary Examiner—C. Fred Rosenbaum
Assistant Examiner—J. L. Kruter
Attorney, Agent, or Firm—Brumbaugh, Graves, Donohue & Raymond

[57]  ABSTRACT

A sheath-type external catheter is provided having upper and lower portions defined by the gauge of the material used to construct the sheath; and a tubular ring applicator. The applicator surrounds the inner surface of the upper portion of the sheath which is everted over the lower portion of the sheath. In constructing the novel catheter/applicator combination, the inner surface of the upper sheath portion is everted over the outside surface of the lower sheath portion. With the catheter in this position, the ring applicator is placed about the lower portion of the sheath so that the inner surface of the ring contacts the inner surface of the upper sheath portion. The everted portion of the sheath is generally longer than the length of the ring member, with a portion of the everted upper sheath extending below the ring.

12 Claims, 1 Drawing Sheet

EXTERNAL CATHETER AND APPLICATOR

BACKGROUND OF THE INVENTION

The present invention relates to an external catheter and applicator combination. Catheters for use in male urinary transport systems are well known and generally comprise an elastic sheath designed to surround the glans and shaft of the penis. The distal end of the sheath is typically, integrally formed with an outlet which is connected to a tube, the opposite end of which communicates with a urine collection reservoir. The present invention makes use of such a catheter, but does so in conjunction with a novel applicator means and thereby provides a novel combination which avoids and/or reduces many of the problems and drawbacks associated with known prior art external sheath-type catheters, and particularly those having an adhesive coating material applied to a portion of the inside surface of the sheath. The principal difficulties with such catheters arise upon application of the catheter to the glans and shaft of the penis and urine leakage due to improper application. For example, when preparing to apply or applying a sheath-type catheter having an adhesive-coated inner surface, care must be initially exercised to ensure that the adhesive inner surfaces of the sheath do not contact one another and that the sheath is evenly applied, without creating pockets, voids or wrinkles. In accordance with the teaching of U.S. Pat. No. 4,540,409, a sheath-type external male catheter having a portion of its internal surface coated with an adhesive material, is combined with a tubular applicator. More specifically, the external catheter is of the type generally described above. The applicator is in the form of a relatively rigid open-ended, tapered tube, the length of which is less than the length of the fully extended sheath, and the diameter of which is slightly greater than the maximum inside diameter of the unstretched sheath. The distal end of the sheath and its outlet and drainage tube are disposed within the tube. The cylindrical body portion of the sheath is everted over a portion of the outside surface of the applicator tube. So arranged, the outside surface of the sheath contacts the outside surface of the applicator tube, with the innerside of the sheath, i.e., the side having the adhesive coating facing outwardly and hence not susceptible of contacting any other surface portion containing the adhesive coating. In applying the catheter, the portion of the sheath which is not everted, i.e., the distal end of the sheath, is placed over the glans and the applicator tube is slideably moved along the penile shaft, thereby causing the everted portion of the sheath to revert so that the inner surface of the sheath and adhesive coating contained thereon contact the penile shaft thereby securing the sheath to the shaft.

While the aforementioned combination applicator sheath catheter tends to avoid the drawback associated wtih the inner adhesive-coated catheter surfaces coming in contact with each other during application, it has been found that the force required to slide the applicator in the reverting step is relatively substantial and as a result is likely to cause the thin elastic sheath to tear. Moreover, as a result of the force required to apply the catheter and the friction between the applicator and the penile shaft, there is an increased potential for the patient to experience an erection, a condition which is exacerbated by the presence of the tube applicator, which to be removed must be slid down the swollen shaft and glans of the penis. Finally, said prior art device generally requires the additional processing step of providing a lubricant on the interior surface of the catheter to facilitate the application of the catheter sheath to the penis. Moreover, the presence of a lubricant adds to the overall problems associated with the application of the external catheter, i.e., removing any lubricant residue.

In accordance with the invention disclosed herein, the conventional sheath-type male catheter is combined in a novel manner with a novel applicator ring, which together renders the application process markedly improved. More specifically, the present invention substantially eliminates any likelihood of tearing the sheath; substantially diminishes the potential for erection since the sheath quickly and smoothly slides over the shaft of the penis; and obviates the need for a lubricant to facilitate application of the sheath.

SUMMARY OF THE INVENTION

The invention disclosed in detail below comprises a sheath-type external catheter, having upper and lower portions defined by the gauge of the material used to construct the sheath; and a tubular ring applicator. The applicator surrounds the inner surface of the upper portion of the sheath which is everted over the lower portion of the sheath. In constructing the novel catheter/applicator combination, the inner surface of the upper sheath portion is everted over the outside surface of the lower sheath portion. With the catheter in this position, the ring applicator is placed about the lower portion of the sheath so that the inner surface of the ring contacts the inner surface of the upper sheath portion. The everted portion of the sheath is generally longer than the length of the ring member, with a portion of the everted upper sheath extending below the ring. In a preferred embodiment, this sheath is reverted over the outside surface of the ring.

Application of the catheter/applicator combination is accomplished simply and easily by placing the glans of the penis within the wide opening of the lower portion of the sheath and gently sliding the ring along the penile shaft. In so doing, the sheath smoothly slides onto the penile shaft. Thereafter, the ring member, which in a further preferred embodiment is a split-ring, is removed from about the shaft without having to subject the patient to further sliding of the ring over the penile shaft.

As stated above, a preferred embodiment of the present invention contemplates the ring element in the form of a split and hinged ring which facilitates both the engagement of the ring around the lower portion of the sheath over which the upper sheath portion is everted; and the disengagement of the ring about the penile shaft after the sheath has been applied to the penile shaft.

In still another preferred embodiment, the split-ring applicator has a flange formed on its proximal end which facilitates movement of the ring along the shaft of the penis, to unroll the sheath.

In a further preferred embodiment of the invention, the inner surface of the upper sheath portion which is everted over the lower sheath portion contains an adhesive coating which is covered by the inner surface of the ring applicator. Said coating is preferably located circumferentially so that the adhesive contacts the penile shaft behind (proximal to) the corona of the glans.

Other features, advantages, objects and improvements, provided by the novel catheter/applicator combination will be apparent from the drawings and the following detailed description of the present invention.

DRAWINGS

DESCRIPTION OF PREFERRED EMBODIMENT

Figure 1:
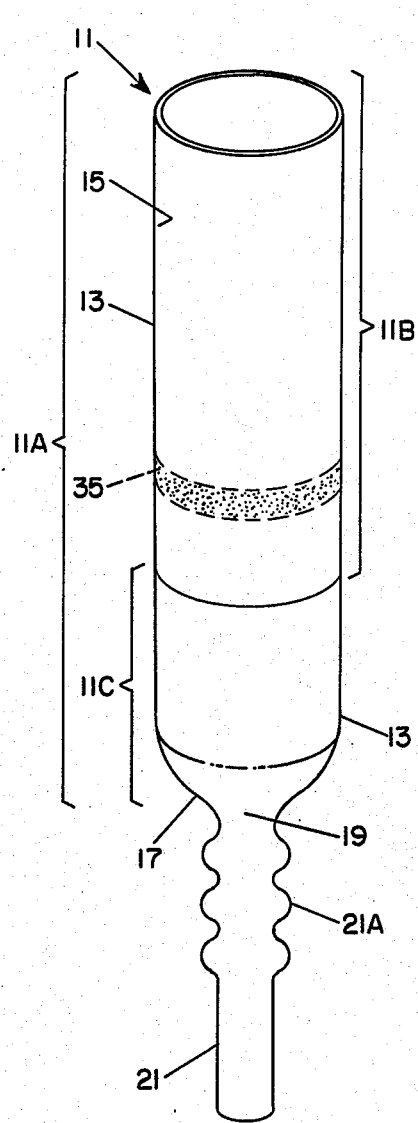
FIG. 1 is a perspective view of a catheter sheath outlet and drainage tube used in the present invention.

The external male urinary catheter, FIG. 1, comprises one of the two principal structural elements of the combination of the present invention. The other element is the applicator ring, illustrated in FIG. 2. With reference to FIG. 1, catheter 11 is formed from a suitable soft, highly elastic, natural or synthetic rubber. Natural latex is preferred, however, elastomers having similar properties may also be used. The catheter includes an elongated, generally cylindrically-shaped, outer sheath 11A having an upper portion 11B and an integral lower portion 11C. Said sheath 11 has an outer wall surface 13 and an inner wall surface 15. The lower portion 11C of sheath 11 is constructed so as to be relatively shape retaining, i.e., the thickness of the wall surfaces are substantially greater than the wall surfaces of the upper portion 11B of sheath 11. For example, the thickness of the wall surfaces of 11B may range from 0.003 to 0.010 inches, while the thickness of the wall surfaces of 11C may be approximately 0.030 inches.

The distal end of the lower sheath portion 11C has a gradually tapered configuration 17 culminating at outlet 19 and transport tube 21, both of which have less of a cylindrical section than the main cylindrical section of sheath 11. Furthermore, as a preferred design feature, the upper portion of transport tube 21 is illustrated as being bulbed 21A, to impart flexibility to the tube 21. Distal sheath end 11C, outlet 19 and tubing 21A are integral and made from the same gauge, i.e., thickness of material. The thickness of tube 21 is approximately 0.040 to 0.060 inches.

The catheter 11 is provided with an internal adhesive coating, illustrated as strip 35. It has been found that to be most effective the adhesive material should be located about the inner circumference of the sheath portion 11B after everting the upper sheath portion 11B over the lower sheath portion 11C. In this position, the adhesive material contacts the penile shaft rearwardly of the corona of the glans. The adhesive coating may be any suitable medical grade, pressure-sensitive adhesive of a type well known in the art. A particularly preferred adhesive coating is the hypo-allergenic acrylic adhesive.

Figure 2:
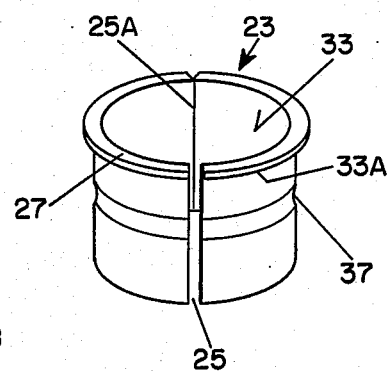
FIG. 2 is a perspective view of a preferred embodiment of an applicator ring.
Figure 3:
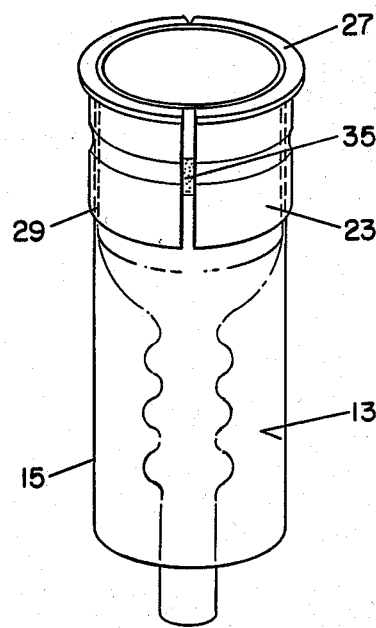
FIG. 3 is a perspective view illustrating the catheter/applicator ring combination with the everted sheath portion extending below the ring.
Figure 4:
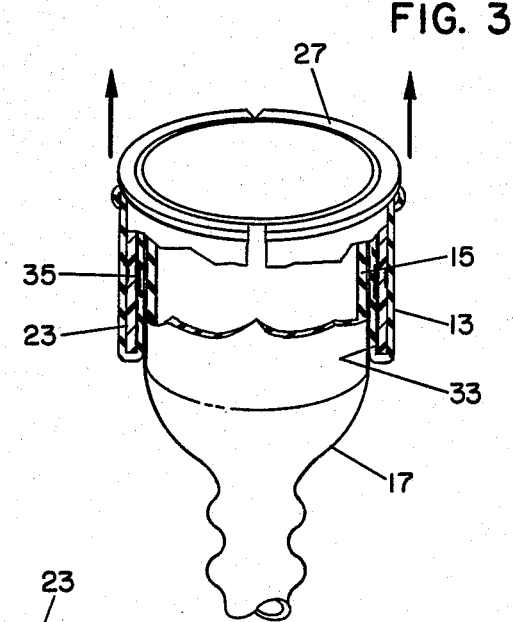
FIG. 4 is an enlarged perspective view of a preferred embodiment of the catheter/applicator combination as it would appear prior to use.
Figure 5:
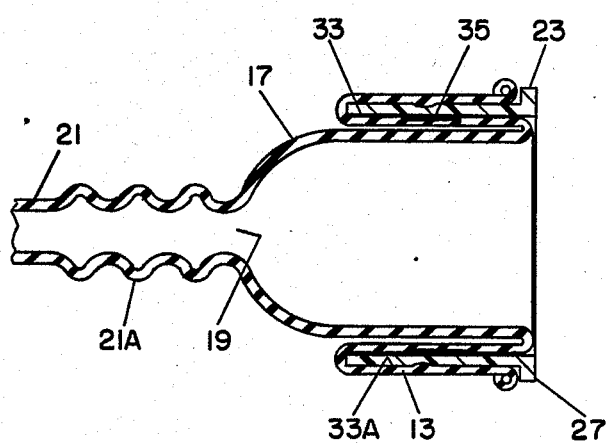
FIG. 5 is an enlarged longitudinal sectional view of the catheter/applicator combination illustrated in FIG. 4.

The second principal component of the combination catheter/applicator of the present invention is ring applicator 23, depicted in FIG. 2 and in combination with sheath 11 in FIGS. 3∝5. For the purposes of the following discussion, reference will primarily be made to FIG. 2. Ring 23 is open at both ends and generally cylindrical in shape, having inner and outer wall surfaces 33 and 33A, respectively. As a prefered embodiment, ring 23 is hinged 25A to provide a split-ring 25 which facilitates both the manufacture/assembly of the novel catheter/applicator ring combination, as well as removal of the ring applicator after application of the sheath to the shaft of the penis. Ring 23 has an inside diameter substantially equal to that of the everted upper sheath portion 11B so as to be capable of surrounding, but not distorting, the unstretched shape of sheath portion 11B. As illustrated, ring 23 is formed with a flange 27 and a circumferential groove 37. Flange 27 provides a convenient surface for griping ring 23 and facilitates movement of the applicator ring along the penile shaft in order to cause sheath 11 to slide upon itself onto the penile shaft. Ring 23 has a lengthwise dimension slightly greater than the width of the adhesive band 35. Groove 37 provides a seat for the rolled elastic sheath portion that is reverted over the outer surface of ring 23. Ring 23 may be made from any suitable materials, e.g., polypropylene, which may result in a smooth-edged, relatively rigid ring structure.

With reference to FIGS. 1 and 3-5, the catheter and ring applicator are assembled as follows. Sheath portion 11B is first everted. In this position, the outer wall 13 of the upper sheath 11B contacts the outer wall surface of the lower sheath portion 11C, with the inner wall surface 15 of sheath portion 11B being disposed over the more rigid lower sheath portion 11C. Adhesive band 35 is circumferentially applied to the inner surface 15 of the everted upper sheath portion 11B which is facing outward. Ring 23 is split open and placed about the everted upper sheath portion, so that the inner wall surface 33 of ring 23 contacts the everted inner wall surface 15 and adhesive 35 applied thereto. Thereafter, the everted upper sheath portion 11B which extends below the inside wall surface 33 of ring 23, as shown in FIG. 3, is reverted over the outer wall surface 33A of ring 23.

Application of the aforesaid combination catheter/applicator ring is effected smoothly and simply by placing the opening of catheter portion 11C over the glans of the penis; lightly griping flange 27 of ring 23; moving the applicator ring 23 along the penile shaft so as to cause sheath 11 to slide upon itself along said shaft, whereby adhesive band 35 is peeled from ring 23 and gently applied to the penile shaft; and, thereafter, splitting open ring 23 and removing it from around the shaft of the penis.

While the foregoing discloses an embodiment of the invention in considerable detail, it will be understood by those skilled in the art that various aspects of the present invention may be modified without departing from the spirit and scope of the invention.

We claim:

1. An external catheter and applicator combination, said catheter comprising an elastic sheath having upper and lower portions and inner and outer surfaces, wherein one end is adapted for transporting urine to a suitable reservoir and the other end is adapted to receive the glans of the penis; an applicator comprising a relatively rigid longitudinally extending ring means having inner and outer surfaces and an inside diameter which is slightly greater than the outside diameter of the lower portion of said sheath; said upper sheath portion extends longitudinally and is everted longitudinally over at least a portion of the outer surface of the lower portion of the outer sheath portion forming an everted outer surface, wherein at least a portion of the inner surface of the ring means contacts a portion of said everted outer everted surface of the upper sheath portion, the lower sheath portion being suitably sized to allow insertion of the penis and wherein when the ring means is slideably moved along the penile shaft said everted inner surface of the upper sheath portion is caused to revert along the penile shaft.

2. The catheter and applicator combination according to claim 1, wherein a portion of the everted sheath extends below the ring and is reverted over the outer surface of said ring.

3. The catheter and applicator combination according to claim 1, wherein the inner sheath surface everted over the lower sheath portion contains an adhesive coating said adhesive being transferred to the penile shaft when said ring is slidably moved along said shaft.

4. The catheter and applicator combination according to claim 1, wherein the upper and lower portions of said sheath are integral and wherein the upper portion is constructed from a thin, stretchable elastic material and the lower portion of said sheath is constructed from a thicker gauge of elastic material such that said lower portion is substantially shape-retaining.

5. The catheter and applicator combination according to claim 1, wherein the distal end of the lower portion of the sheath is gradually tapered to form an outlet and tube for transporting urine to said reservoir.

6. The catheter and applicator combination according to claim 1, wherein the inner circumferential surface of the lower sheath portion contains a pressure-sensitive adhesive coating.

7. An external catheter and applicator combination, said catheter comprising an elastic sheath having upper and lower portions and inner and outer surfaces, wherein one end is adapted for transporting urine to a suitable reservoir and the other end is adapted to receive the glans of the penis; an applicator comprising a relatively rigid split, hinged ring having inner and outer surfaces and an inside diameter which is slightly greater than the outside diameter of the lower portion of said sheath; said upper sheath portion being everted over the outer surface of the lower sheath portion and said everted upper sheath portion being surrounded by said ring so that the inner ring surface contacts a portion of the everted inner sheath surface; whereby when the glans of the penis is inserted into the end of the sheath adapted to receive the same and said ring is slidably moved along the shaft of the penis, the everted portion of the said sheath reverts along said shaft.

8. The catheter and applicator combination according to claim 7, wherein the length of said split and hinged ring is sufficient to at least cover the adhesive strip; and wherein one end of said ring has a flange and the outside surface of said ring has a circumferential groove.

9. An external catheter and applicator combination, said catheter comprising an elastic sheath having upper and lower portions and inner and outer surfaces, wherein the distal end of the lower portion is adapted for transporting urine to a suitable reservoir and the proximal end of said lower portion is adapted to receive the glans of the penis; an applicator comprising a relatively rigid longitudinally extending ring means having inner and outer surfaces and an inside diameter which is slightly greater than the outside diameter which is slightly greater than the outside diameter of the lower portion of said sheath; said upper sheath portion extends longitudinally and is everted longitudinally over at least a portion of the outer surface of the lower sheath portion forming an outer everted surface, wherein at least a portion of the inner surface of the ring means contacts a portion of said everted outer everted surface of the upper sheath portion, the lower sheath portion being suitably sized to allow insertion of the penis and wherein when the ring means is slideably moved along the penile shaft said everted inner surface of the upper sheath portion is caused to revert along the penile shaft.

10. The catheter and applicator combination according to claim 9, wherein a portion of the everted sheath extends past the ring toward the lower end of the sheath and is reverted over the outer surface of said ring in a direction away from the lower end of the sheath.

11. The catheter and applicator combination according to claim 9, wherein a portion of the inner surface of the upper sheath portion everted over the lower sheath portion is coated with an adhesive, at least a portion of said adhesive being in releasable contact with the inner surface of said ring such that said adhesive is transferred to the penile shaft when said ring is slidably moved along said shaft.

12. The catheter and applicator combination according to claim 9, wherein the inner sheath portion is coated with an adhesive, said adhesive being in releasable contact with the inner surface of the ring; and wherein the inner surface of the ring extends along the everted inner surface of the upper sheath portion sufficiently to at least cover said adhesive.

* * * * *

UNITED STATES PATENT AND TRADEMARK OFFICE
CERTIFICATE OF CORRECTION

PATENT NO. : 4,784,655
DATED : November 15, 1988
INVENTOR(S) : Campion et al.

It is certified that error appears in the above-identified patent and that said Letters Patent is hereby corrected as shown below:

Col. 3, line 65, "3∝5" should read --3-5--;

Col. 4, line 1, "prefered" should read --preferred--;

Col. 4, line 12, "griping" should be --gripping--;

Col. 4, line 42, "griping" should be --gripping--;

Col. 6, bridging lines 16 and 17, delete "which is slightly greater than the outside diameter".

Signed and Sealed this

Eleventh Day of July, 1989

Attest:

DONALD J. QUIGG

*Attesting Officer*   *Commissioner of Patents and Trademarks*